United States Patent
Allen et al.

(10) Patent No.: US 10,971,254 B2
(45) Date of Patent: Apr. 6, 2021

(54) MEDICAL CONDITION INDEPENDENT ENGINE FOR MEDICAL TREATMENT RECOMMENDATION SYSTEM

(71) Applicant: International Business Machines Corporation, Armonk, NY (US)

(72) Inventors: Corville O. Allen, Morrisville, NC (US); Thomas J. Eggebraaten, Rochester, MN (US); Mark G. Megerian, Rochester, MN (US); Richard J. Stevens, Monkton, VT (US)

(73) Assignee: International Business Machines Corporation, Armonk, NY (US)

( * ) Notice: Subject to any disclaimer, the term of this patent is extended or adjusted under 35 U.S.C. 154(b) by 435 days.

(21) Appl. No.: 15/262,311

(22) Filed: Sep. 12, 2016

(65) Prior Publication Data

US 2018/0075194 A1  Mar. 15, 2018

(51) Int. Cl.
*G16H 10/60* (2018.01)
*G16H 50/30* (2018.01)
(Continued)

(52) U.S. Cl.
CPC ............ *G16H 10/60* (2018.01); *G16H 20/00* (2018.01); *G16H 50/20* (2018.01); *G16H 50/30* (2018.01); *G16H 70/20* (2018.01); *G16H 70/60* (2018.01)

(58) Field of Classification Search
CPC ....... G06F 19/325; G06F 19/00; G16H 10/60; G16H 50/30
See application file for complete search history.

(56) References Cited

U.S. PATENT DOCUMENTS 5,839,438 A * 11/1998 Graettinger ............. A61B 5/00
                                                    600/300
6,017,331 A    1/2000 Watts et al.
(Continued)

OTHER PUBLICATIONS

"Quantitative Pros and Cons" website printout, archived on Aug. 13, 2016, 4 pages (Year: 2016).*
(Continued)

*Primary Examiner* — Janice A Mooneyham
*Assistant Examiner* — Steven G Sanghera
(74) *Attorney, Agent, or Firm* — Francis Lammes; Stephen J. Walder, Jr.; William J. Stock

(57) ABSTRACT

Mechanisms are provided which configure a medical treatment recommendation system to implement a medical condition independent treatment recommendation model. The medical condition independent treatment recommendation model operates on medical condition independent scoring features that are independent of any specific medical condition. The mechanisms configure the medical treatment recommendation system to receive a medical condition cartridge providing at least one medical condition specific evaluation feature that is specific to a medical condition, and process patient information based on a combination of an application of the at least one medical condition specific evaluation feature, and an execution of the medical condition independent treatment recommendation model of the medical treatment recommendation system, to generate a treatment recommendation for a patient medical condition associated with the patient. The mechanisms then output the treatment recommendation for the patient.

20 Claims, 6 Drawing Sheets

(51) Int. Cl.
    *G16H 70/60*       (2018.01)
    *G16H 50/20*       (2018.01)
    *G16H 20/00*       (2018.01)
    *G16H 70/20*       (2018.01)

(56) References Cited

U.S. PATENT DOCUMENTS

| | | | | |
|---|---|---|---|---|
| 6,063,028 | A * | 5/2000 | Luciano | G16H 50/50 600/300 |
| 6,248,063 | B1 * | 6/2001 | Barnhill | G01N 33/50 600/300 |
| 7,233,892 | B2 | 6/2007 | Brill et al. | |
| 8,275,803 | B2 | 9/2012 | Brown et al. | |
| 8,473,489 | B1 | 6/2013 | Lasko et al. | |
| 8,868,472 | B1 * | 10/2014 | Lin | G06N 20/00 706/12 |
| 9,298,880 | B2 | 3/2016 | Vilsmeier et al. | |
| 9,336,497 | B2 | 5/2016 | Baughman et al. | |
| 9,779,611 | B1 | 10/2017 | Krayer et al. | |
| 10,340,034 | B2 | 7/2019 | Hyde et al. | |
| 2003/0105638 | A1 | 6/2003 | Taira | |
| 2003/0163353 | A1 * | 8/2003 | Luce | G06F 19/3418 705/2 |
| 2007/0094188 | A1 | 4/2007 | Pandya et al. | |
| 2008/0171916 | A1 | 7/2008 | Feder et al. | |
| 2008/0201280 | A1 | 8/2008 | Martin et al. | |
| 2009/0006131 | A1 * | 1/2009 | Unger | G06F 19/321 705/3 |
| 2009/0156906 | A1 | 6/2009 | Liebman et al. | |
| 2009/0287678 | A1 | 11/2009 | Brown et al. | |
| 2010/0169219 | A1 | 7/2010 | Sellers et al. | |
| 2010/0234236 | A1 | 9/2010 | Cohen et al. | |
| 2011/0046979 | A1 | 2/2011 | Tulipano et al. | |
| 2011/0066587 | A1 | 3/2011 | Ferrucci et al. | |
| 2011/0125734 | A1 | 5/2011 | Duboue et al. | |
| 2012/0016690 | A1 * | 1/2012 | Ramarajan | G06Q 50/22 705/2 |
| 2012/0178179 | A1 | 7/2012 | Kim et al. | |
| 2013/0007055 | A1 | 1/2013 | Brown et al. | |
| 2013/0018652 | A1 | 1/2013 | Ferrucci et al. | |
| 2013/0066886 | A1 | 3/2013 | Bagchi et al. | |
| 2013/0102087 | A1 | 4/2013 | Kasdan et al. | |
| 2013/0132312 | A1 | 5/2013 | Lee et al. | |
| 2013/0226616 | A1 | 8/2013 | Nigam et al. | |
| 2014/0046889 | A1 | 2/2014 | Biem et al. | |
| 2014/0058738 | A1 | 2/2014 | Yeskel | |
| 2014/0073882 | A1 | 3/2014 | Choi et al. | |
| 2014/0081898 | A1 | 3/2014 | Saigal et al. | |
| 2014/0113263 | A1 | 4/2014 | Jarrell et al. | |
| 2014/0337051 | A1 | 11/2014 | Karpf et al. | |
| 2014/0365232 | A1 | 12/2014 | Sadeghi | |
| 2015/0019241 | A1 | 1/2015 | Bennett et al. | |
| 2015/0066537 | A1 | 3/2015 | Sheffer et al. | |
| 2015/0066539 | A1 | 3/2015 | Sheffer et al. | |
| 2015/0118661 | A1 | 4/2015 | Haruta et al. | |
| 2015/0302167 | A1 | 10/2015 | Vali et al. | |
| 2015/0356270 | A1 | 12/2015 | Devarakonda et al. | |
| 2015/0363559 | A1 * | 12/2015 | Jackson | G16H 10/20 705/2 |
| 2015/0370982 | A1 | 12/2015 | Zien et al. | |
| 2016/0063212 | A1 | 3/2016 | Monier et al. | |
| 2016/0070867 | A1 | 3/2016 | Zhang et al. | |
| 2016/0078039 | A1 | 3/2016 | Baughman et al. | |
| 2016/0110501 | A1 | 4/2016 | Allen et al. | |
| 2016/0358290 | A1 | 12/2016 | Chiu et al. | |
| 2017/0262587 | A1 | 9/2017 | Agarwal et al. | |

OTHER PUBLICATIONS

"LarKC: the Large Knowledge Collider", http://www.larkc.org/overview/index.html, Accessed from the Internet on May 12, 2016, 4 pages.

Baum, Stephanie, "Could an EMR plugin using big data help physicians make diagnosis more efficient?", MedCityNews, Jul. 9, 2013, 9 pages.

Gotz, David et al., "IDCA: A Platform for Intelligent Care Delivery Analytics", Proceedings of AMIA Annual Symposium, Nov. 2012, 12, 10 pages.

High, Rob, "The Era of Cognitive Systems: An Inside Look at IBM Watson and How it Works", IBM Corporation, Redbooks, Dec. 12, 2012, 16 pages.

McCord, M.C. et al., "Deep parsing in Watson", IBM J. Res. & Dev. vol. 56 No. 3/4 Paper 3, May/Jul. 2012, pp. 3:1-3:15.

Sjobergh, Jonas et al., "Visualizing Clinical Trial Data Using Pluggable Components", 16th International Conference on Information Visualization, Jul. 11-13, 2012, 6 pages.

Wall, Dennis P. et al., "Genotator: A disease-agnostic tool for genetic annotation of disease", BMC Medical Genomics, Oct. 2010, 10 pages.

Yuan, Michael J., "Watson and healthcare, How natural language processing and semantic search could revolutionize clinical decision support", IBM developerWorks, IBM Corporation, Apr. 12, 2011, 14 pages.

Miotto, Riccardo et al., "Deep Patient: An Unsupervised Representation to Predict the Future of Patients from the Electronic Health Records,", Scientific Reports, May 17, 2016, 10 pages.

List of IBM Patents or Patent Applications Treated as Related, May 2, 2017, 2 pages.

"The Era of Cognitive Systems: An inside look at IBM Watson and how it works", IBM Corporation, IBM Software Group, Whitepaper, IBM Watson Solutions, Sep. 2012, 19 pages.

Choi, Wonjun et al., "HerDing: herb recommendation system to treat diseases using genes and chemicals", Oxford University Press, Jan. 2016, 7 pages.

Deleger, Louise et al., "Building Gold Standard Corpora for Medical Natural Language Processing Tasks", AMIA Annual Symposium Proceedings 2012, Nov. 3, 2012, pp. 144-153.

Denmer-Fushman, Dina et al., "What can Natural Language Processing do for Clinical Decision Support?", J Biomed. Inform., 42(5), Oct. 2009, 29 pages.

Hussein, Asmaa et al., "Accurate and Reliable Recommender System for Chronic Disease Diagnosis", Global Health 2012: The First International Conference on Global Health Challenges, Oct. 2012, pp. 113-118.

Lim, Thean Pheng et al., "Recommender System for Personalised Wellness Therapy", International Journal of Advanced Computer Science and Applications (IJACSA), vol. 4, No. 9, Oct. 2013, pp. 54-60.

Mahdavi, Meisamshabanpoor and Mehregan, "Implementation of a Recommender System on Medical Recognition and Treatment", International Journal of e-Education, e-Business, e-Management and e-Learning, vol. 2, No. 4, Aug. 2012, pp. 315-318.

Sodsee, Sunantha et al., "Evidence-based Medical Recommender Systems: A Review", International Journal of Information Processing and Management, vol. 4, No. 6, Sep. 2013, pp. 114-120.

Wiesner, Martin et al., "Health Recommender Systems: Concepts, Requirements, Technical Basics and Challenges", International Journal of Environmental Research and Public Health, Mar. 3, 2014, 28 pages.

* cited by examiner

MEDICAL CONDITION INDEPENDENT ENGINE FOR MEDICAL TREATMENT RECOMMENDATION SYSTEM

BACKGROUND

The present application relates generally to an improved data processing apparatus and method and more specifically to mechanisms for providing a medical condition independent engine for implementing a medical treatment recommendation system.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, where the at least one memory comprises instructions which are executed by the at least one processor to specifically configure the data processing system to implement a medical treatment recommendation system. The method comprises configuring, in the data processing system, the medical treatment recommendation system to implement a medical condition independent treatment recommendation model. The medical condition independent treatment recommendation model is trained on, and operates on, medical condition independent scoring features that are independent of any specific medical condition. The method further comprises configuring, in the data processing system, the medical treatment recommendation system to receive a medical condition cartridge that provides at least one medical condition specific evaluation feature that is specific to a particular medical condition. Moreover, the method comprises processing, by the data processing system, patient information for a patient based on application of a combination of the at least one medical condition specific evaluation features, associated with the medical condition cartridge, and an execution of the medical condition independent treatment recommendation model of the medical treatment recommendation system, to generate at least one treatment recommendation for a patient medical condition associated with the patient. In addition, the method comprises outputting, by the data processing system, the at least one treatment recommendation for the patient.

In some optional illustrative embodiments, application of the at least one medical condition specific evaluation feature generates, for the particular medical condition, at least one medical condition independent scoring feature of the medical condition independent scoring features of the medical condition independent treatment recommendation model in a manner that is specific to the particular medical condition. Moreover, in other optional illustrative embodiments the medical condition cartridge receives patient information as input and application of the at least one medical condition specific evaluation feature evaluates factors in the patient information to generate the at least one medical condition independent scoring feature in a manner specific to a combination of the specific medical condition and a candidate treatment. Optionally, the factors may comprise one or more factors selected from the set comprising patient factors defining characteristics of the patient and medical condition factors defining characteristics of the patient medical condition.

In some optional illustrative embodiments, processing patient information for the patient comprises: receiving, by the medical treatment recommendation system, an electronic medical record (EMR) of the patient comprising patient factors representing a medical state of the patient; executing, by the medical treatment recommendation system, logic that applies at least one medical condition specific evaluation feature of the medical condition cartridge to generate a medical condition independent scoring feature for a combination of the specific medical condition, a candidate treatment, and the patient factors of the patient, based on an aggregation function specified in the medical condition cartridge; and applying, by the medical treatment recommendation system, the medical condition independent treatment recommendation model to the medical condition independent scoring feature to generate a candidate treatment recommendation confidence score for the candidate treatment.

In still other optional illustrative embodiments, processing the patient information comprises executing logic that applies at least one medical condition specific evaluation feature of the medical condition cartridge to: perform calculations that are specific to the particular medical condition and a particular candidate treatment, to generate medical condition specific score values; and apply one or more aggregation operations to one or more subsets of the medical condition specific score values to generate aggregation values, each aggregation value corresponding to one of the medical condition independent scoring features of the medical condition independent treatment recommendation model. In some optional illustrative embodiments, the medical condition cartridge comprises multiple different instances medical condition specific evaluation features, each instance being associated with the particular medical condition but being further associated with a different candidate treatment for the particular medical condition.

In still further optional illustrative embodiments, the calculations operate on patient factors that provide characteristics of the patient, medical condition factors that characterize the particular medical condition, and candidate treatment factors characterizing aspects of the candidate treatment. Moreover, in some optional illustrative embodiments, the calculations operate to evaluate patient specific characteristics, obtained from an electronic medical record associated with the patient, with regard to weighted variables in the at least one medical condition specific evaluation feature. Furthermore, in some optional illustrative embodiments, each aggregation operation of the one or more aggregation operations map an aggregate value of a subset of the medical condition specific score values to a corresponding medical condition independent scoring feature. In some illustrative embodiments, at least two aggregation operations in the one or more aggregation operations operate on a different subset of the medical condition specific score values.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

Thus, one or more of the illustrative embodiments provide mechanisms for implementing a medical condition independent or agnostic treatment recommendation system that is trained using a relatively small set of features or factors that are not medical condition specific. All of the medical condition specific logic is moved out of the feature set used to train the system and instead is provided in medical condition specific cartridges. These cartridges are provided in a pluggable manner such that they may be utilized to customize the operation of the system to particular medical conditions. Such customization may be done on a dynamic basis based on the particular classes or domains of medical conditions for which a patient is being considered. In this way, the system may be trained more easily and with less outlay of resources, especially with regard to training data sets.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
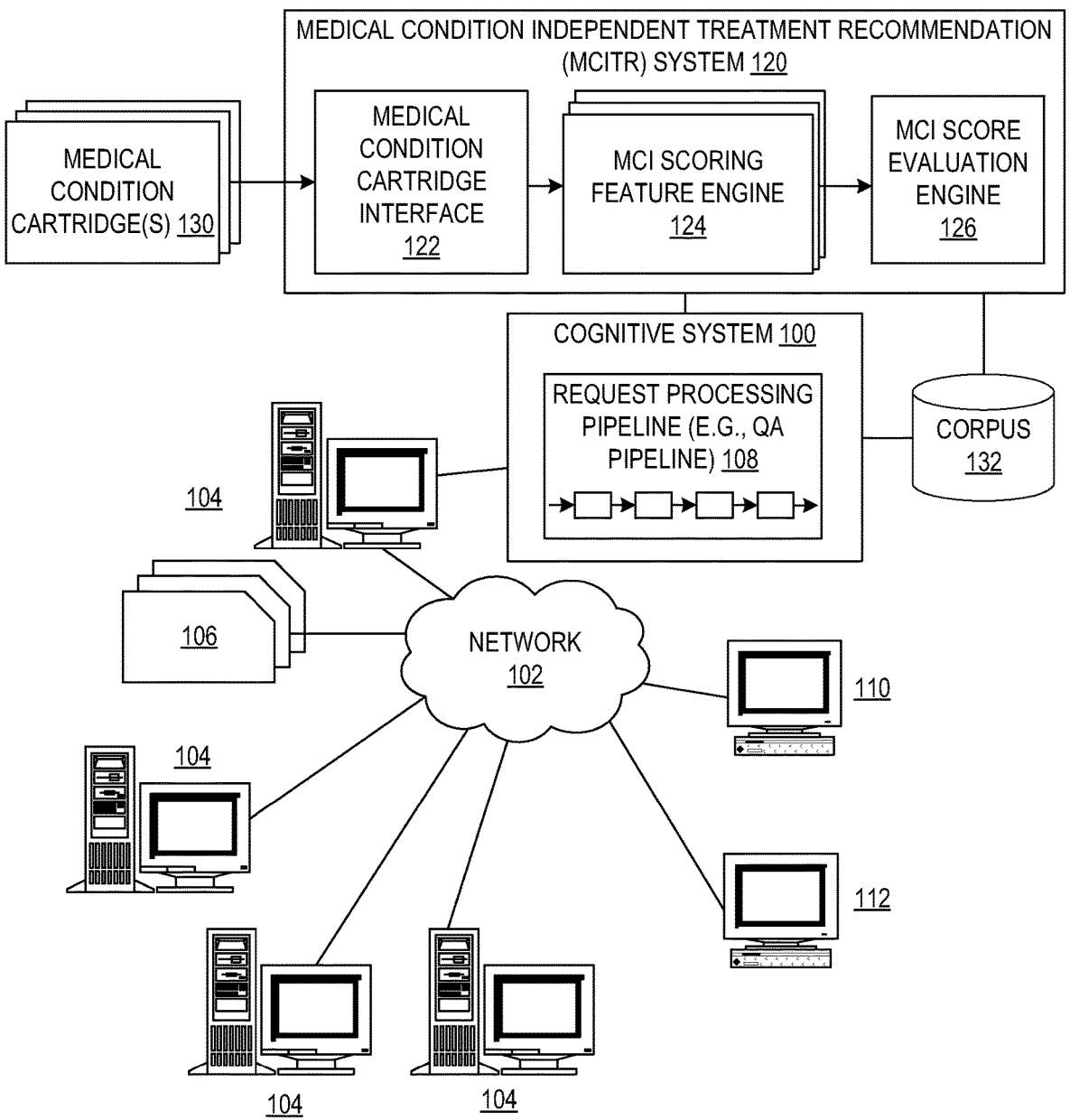
FIG. 1 depicts a schematic diagram of one illustrative embodiment of a cognitive healthcare system in a computer network.

The strengths of current medical diagnosis, patient health management, and patient treatment recommendation systems are that they can improve medical practitioners' diagnostic hypotheses, can help medical practitioners avoid missing important diagnoses, and can assist medical practitioners with determining appropriate treatments for specific diseases. However, current systems still suffer from significant drawbacks which should be addressed in order to make such systems more accurate and usable for a variety of healthcare applications as well as more representative of the way in which human healthcare practitioners diagnose and treat patients. In particular, one drawback of current systems is that they are designed, trained, and configured for use with a small predefined set of medical conditions and/or for a particular subset of medical institutions/practitioners.

For example, medical treatment recommendation systems must be trained and configured to provide treatment recommendations based on machine learning for each possible medical condition and corresponding treatment with which they are intended to operate. When building a treatment recommendation system, initially a set of training cases may be utilized that represents the treatment practices of a particular institution and/or set of doctors for a particular medical condition. This training set forms the basis of a ground truth that the treatment recommendation system strives to replicate through the machine learning process. Through feature engineering, machine learning, iterative improvements, and ongoing knowledge transfer with human subject matter experts, the system is trained to be able to achieve high levels of accuracy in matching the ground truth. If the treatment recommendation system has the proper inputs that are extracted from a subsequent case, e.g., patient electronic medical records (EMRs), either via natural language processing against unstructured text, or directly from structured patient attributes, the treatment recommendation system applies the same considerations as the human subject matter expert as specified through the training, and the treatment recommendation system has the correct domain of possible answers, the treatment recommendation system can approximate the thinking of the subject matter experts (SMEs) since the machine learning process will apply appropriate weights to the various scoring features that have been developed through the training of the system.

This training of the treatment recommendation system works well for individual combinations of medical conditions and their associated treatments. However, if a treatment recommendation system is to support treatment recommendation operations for a large number of different medical conditions, then the treatment recommendation system would need to be trained for each separate medical condition, e.g., disease or other medical malady. In other words, treatment recommendation systems are trained using a very disease-specific and patient attributes-specific based training that results in a complex model with a requirement for a large volume of training cases. For example, there may be features of lung-platinum-therapy, liver-dysfunction-comorbidity, or alopecia-avoidance, or any other very specific medical condition, treatment, and patient attributes and all of these features and their possible combinations must be considered during training of the treatment recommendation system so that future treatment recommendations may be made accurately when encountering similar features or combinations of features in subsequent cases.

The requirements for such large scale and complex training of treatment recommendation systems leads to a large outlay of resources to build and train these systems, or if such large amounts of resources are not invested, then this leads to systems that have overly limited use. Moreover, the resulting trained system is still inflexible to new treatments, medical conditions, and patient attributes being introduced, new correlations of such features being discovered, or the like, since this would require retraining of the treatment recommendation system.

To address these drawbacks, the illustrative embodiments provide mechanisms for providing a treatment recommendation system framework that allows for a medical condition independent, or agnostic, treatment recommendation engine which operates on medical condition independent scoring features. That is, in some illustrative embodiments, the medical condition independent scoring features comprise an inclusion criteria score feature, an exclusion criteria score feature, and a preference score feature. The specific evaluation features for a particular medical condition are implemented in a pluggable "cartridge" that indicates the manner by which input factors, such as patient attributes, treatment features, medical condition features, and the like, are aggregated into the various medical condition independent scoring features. Thus, the medical condition independent treatment recommendation engine may be trained in a manner that is independent of the medical conditions, based on the medical condition independent scoring features, and therefore, does not require retraining every time there is a new medical condition, medical knowledge, or treatment option introduced, or correlation of factors determined to exist. The pluggable cartridges may be readily modified and integrated into the medical condition independent treatment recommendation system's framework without having to provide extensive training and large numbers of training cases to cover all possibilities of combinations of factors.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for implementing a medical condition independent treatment recommendation system that may be trained using medical condition independent scoring features and pluggable cartridges for medical conditions that map specific features associated with the medical condition, patients, and treatments, to these medical condition independent scoring features. The medical condition independent treatment recommendation system is trained, for example, to weight medical condition independent scoring features based on the relative importance of the medical condition independent scoring features to a particular diagnosis and treatment for the diagnosis. The medical condition independent scoring features aggregate medical condition specific features into an abstraction of these medical condition specific features, and this aggregation is used by the medical condition independent treatment recommendation system to select a possible treatment for the patient based on its medical condition independent training and medical condition specific information provided in a pluggable cartridge for the medical condition.

Thus, the set of features that are actually used in the machine learning model of the medical condition independent treatment recommendation system are few and medical condition independent. All of the medical condition specific evaluation features are moved out of the feature set of the machine learning model and placed into the medical condition specific cartridge for use with scoring logic, which may be provided as part of the medical condition specific cartridge as well, that applies these medical condition specific evaluation features to patient information and feeds into the aggregate scoring features of the medical condition independent machine learning model of the treatment recommendation system, i.e. this medical condition specific information is provided in the pluggable cartridges and defines the way in which various features are to be aggregated to generate a medical condition independent scoring feature that is used by the medical condition independent treatment recommendation system. The result is that the medical condition independent treatment recommendation system may be trained in an independent manner such that the same base machine learning model may be reused for various medical conditions, including new medical conditions that the system was not previously exposed to, without having to perform extensive re-training of the system and without having to introduce large numbers of training data sets to perform such training.

As noted above, the medical condition independent treatment recommendation system provides a pluggable framework in which medical condition specific cartridges are "plugged into" to thereby provide medical condition specific logic that is usable to assist in generating treatment recommendations for specific medical conditions. The pluggable medical condition cartridge includes a set of treatments and the set of attributes for a specific medical condition. The pluggable medical condition cartridge may also include a set of disease specific derived attributes and exclusion and inclusion criteria or factors. The pluggable medical condition cartridge mechanisms produce values for these sets of treatments, feature scores for the sets of treatments, and maps feature scores for the sets of treatments to the medical condition independent set of scores. For example, some derived attributes for the medical condition Gastrointestinal Stromal Cancer may include upper_intestine_nonresectable, left_colic_flexure, and mesenchymal. This set of disease specific derived attributes may be mapped into, or otherwise classified as, a medical condition specific scoring feature of "resectable tumor" score, for example. This "resectable tumor" score may in turn be classified or mapped into a medical condition independent scoring feature of an "inclusion criteria" score for a medical treatment of chemotherapy, with this score being given a relatively higher weighting so as to first shrink the tumor, such that it becomes resectable, relative to another medical condition independent scoring feature associated with another regimen to remove the stromal tumor.

Thus, the illustrative embodiments provide mechanisms in which techniques, e.g., structure and/or non-structured content analysis logic, such as natural language processing logic, are provided to extract and/or derive a set of attributes from the medical condition treatment documentation, such as medical treatment guidelines and the like, for each medical treatment, in a plurality of medical treatments, for each medical condition, in a plurality of medical conditions. This extracted/derived set of attributes is used to generate a set of medical treatments that are specific to a medical condition in conjunction with logic/criteria for performing medical condition specific scoring of candidate treatments, which together constitutes a medical condition cartridge.

The mechanisms of the illustrative embodiments provide logic for performing medical condition specific scoring for each candidate medical treatment of a particular medical condition. The features scored for the medical condition specific scoring are aggregated, using medical condition independent mapping logic, into a set of medical condition independent scoring features which may then be provided to a medical condition independent score evaluation engine for use in selecting a medical treatment for treating the medical condition of a patient. The medical condition independent score evaluation logic is separately trainable from the medical condition specific scoring logic provided in the medical condition specific cartridge and is trained in a non-medical condition specific manner.

For example, for a Cisplatin-Hearing Grade exclusion rule provided in a medical condition cartridge for lung cancer, medical condition specific logic is provided that is specific for lung cancer cases (specific medical condition) and gives a negative score to any medical treatment containing Cisplatin when a patient has poor hearing (an attribute for lung cancer). As another example of medical condition specific scoring logic consider a Docetaxel-Neuropathy exclusion rule which is applied to breast cancer cases and gives a negative score to the Docetaxel treatment when the patient has peripheral neuropathy. In a more traditional machine learning system, these would be separate features in a general model. In the illustrative embodiments, however, these two (and many other) logic rules get combined into a medical condition independent scoring of "Exclusion Criteria Score."

The medical condition independent score mapping logic of the illustrative embodiments applies a medical condition independent model to the medical condition specific scores, generated for various medical condition treatments being evaluated to, thereby combine and weight the feature scores for the candidate treatments being evaluated to compute a single final score for each candidate treatment. After this process runs for each candidate treatment, a set of medical condition independent treatment scores is generated which can then be used to rank candidate treatments relative to one another and a final treatment selected as a treatment recommendation. The selected treatment may be, for example, the candidate treatment with the highest score. In some cases, candidate treatments may be classified into different categories of treatment preference depending on their relative ranking, e.g., assigned to categories of "Preferred treatments," "For consideration treatments," and "Not recommended treatments."

Figure 2:
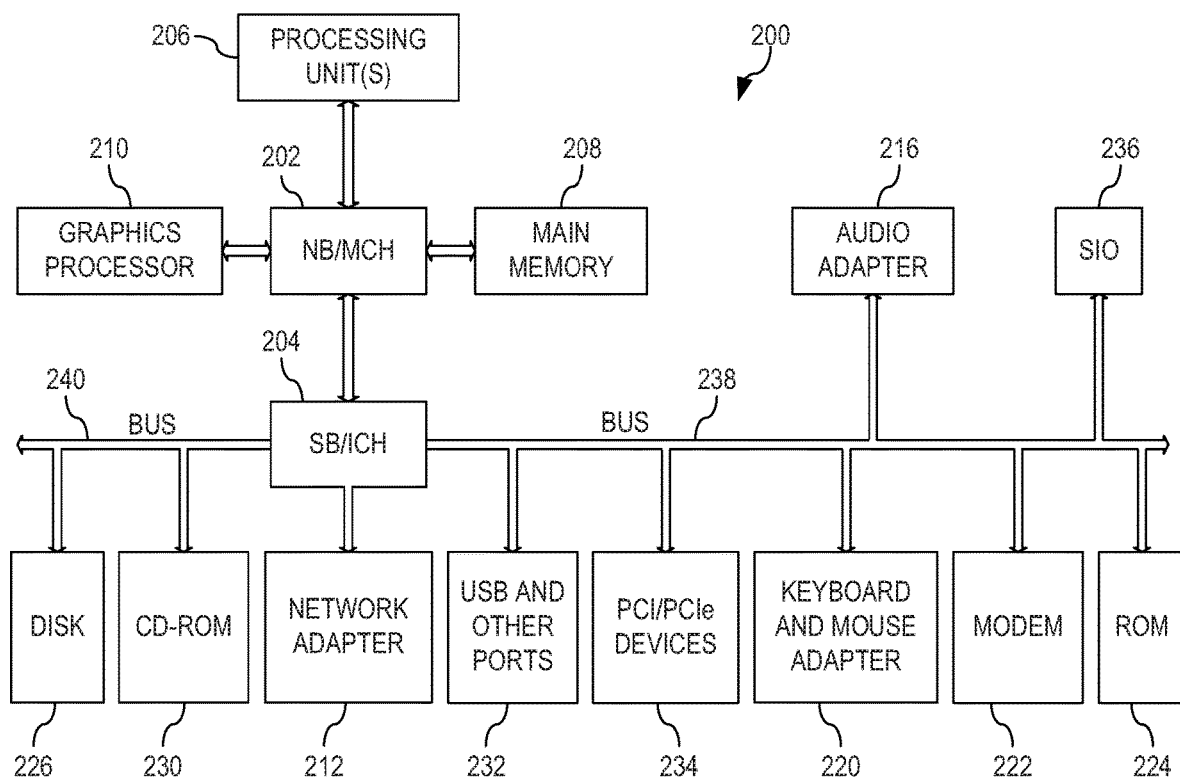
FIG. 2 is a block diagram of an example data processing system in which aspects of the illustrative embodiments are implemented.
Figure 3:
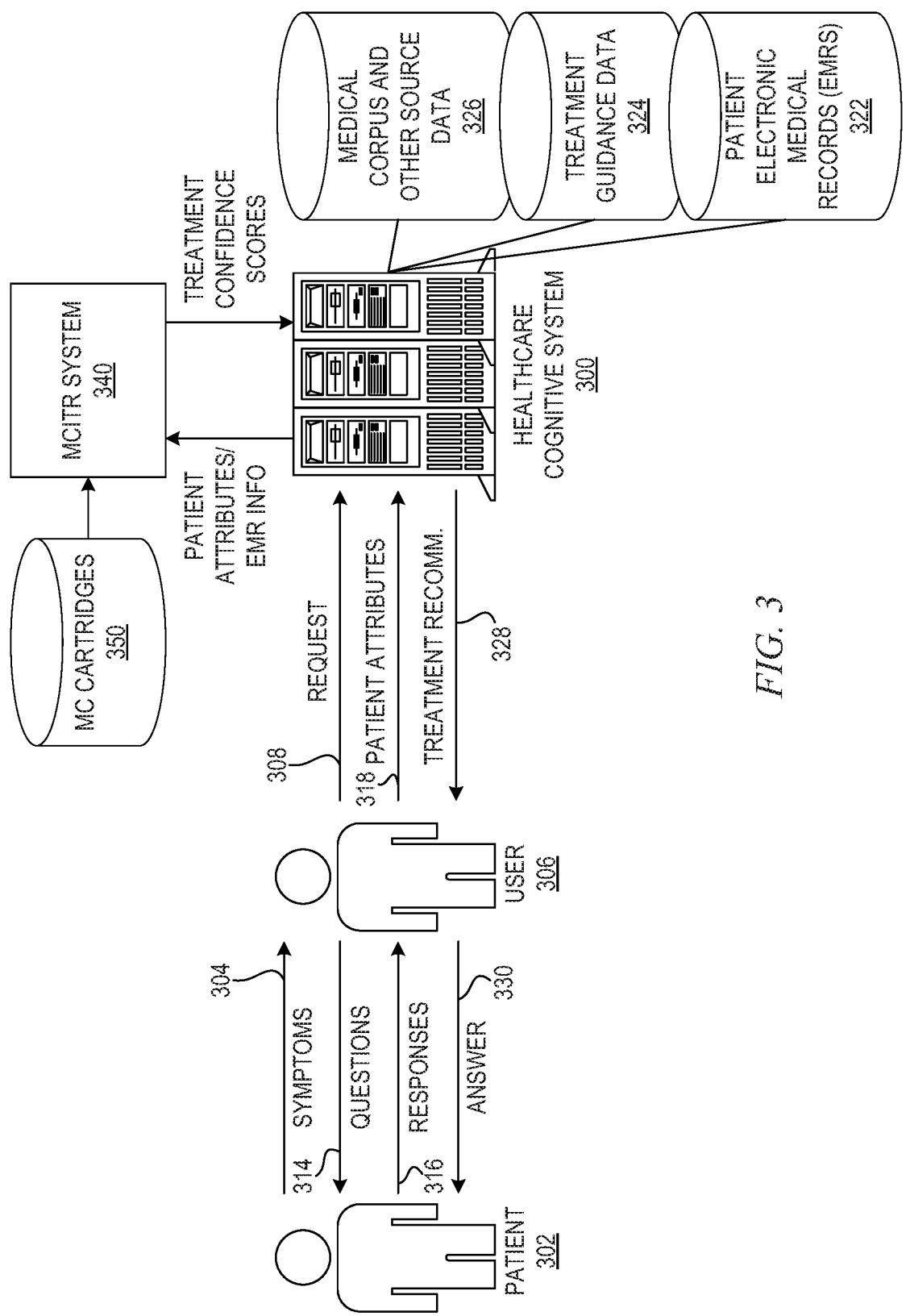
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing medical treatment recommendations for patients based on their specific features as obtained from various sources, e.g., patient electronic medical records (EMRs), patient questionnaires, etc. In particular, the mechanisms of the present invention provide a medical condition independent treatment recommendation system that is trained in a medical condition independent manner with pluggable medical condition specific cartridges providing the medical condition specific logic for customizing the medical condition independent treatment recommendation system to particular medical conditions and their treatments being considered for the patient.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical condition domain (e.g., various types of blood diseases) while another request processing pipeline may be trained to answer input requests in another medical condition domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input questions to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?", the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to providing a medical condition independent treatment recommendation system which may receive an input question regarding the recommended treatment for a specific patient and may utilize the QA pipeline mechanisms to evaluate patient information and other medical information in one or more corpora of medical information to determine the most appropriate treatment for the specific patient. More specifically, the illustrative embodiments provide such a treatment recommendation system that is trained using medical condition independent scoring features which are used in a medical condition independent machine learning model to train the treatment recommendation system. The medical condition independent treatment recommendation system may be customized to one or more specific medical conditions by the way of the ingestion of one or more pluggable medical condition specific cartridges that provide the medical condition specific logic mapping specific features to specific medical condition independent scoring features of the medical condition independent treatment recommendation (MCITR) system. The MCITR system may augment the scoring and ranking of candidate answers, e.g., candidate treatment recommendations, which are provided by the QA pipeline, for example.

Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding
Ingest and process vast amounts of structured and unstructured data
Generate and evaluate hypothesis
Weigh and evaluate responses that are based only on relevant evidence
Provide situation-specific advice, insights, and guidance
Improve knowledge and learn with each iteration and interaction through machine learning processes
Enable decision making at the point of impact (contextual guidance)
Scale in proportion to the task
Extend and magnify human expertise and cognition
Identify resonating, human-like attributes and traits from natural language
Deduce various language specific or agnostic attributes from natural language
High degree of relevant recollection from data points (images, text, voice) (memorization and recall)
Predict and sense with situational awareness that mimic human cognition based on experiences
Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to cognitive system which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm performed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these question and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question processing and answer generation (QA) functionality for one or more cognitive system users via their respective computing devices 110-112. Other embodiments of the cognitive system 100 may be used with components, systems, subsystems, and/or devices other than those that are depicted herein.

The cognitive system 100 is configured to implement a QA pipeline 108 that receive inputs from various sources. For example, the cognitive system 100 receives input from the network 102, a corpus of electronic documents 106, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 106 for use as part of a corpus of data with the cognitive system 100. The document includes any file, text, article, or source of data for use in the cognitive system 100. QA system users access the cognitive system 100 via a network connection or an Internet connection to the network 102, and input questions to the cognitive system 100 that are answered by the content in the corpus of data 106. In one embodiment, the questions are formed using natural language. The cognitive system 100 parses and interprets the question via a QA pipeline 108, and provides a response to the cognitive system user, e.g., client device 110, containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the QA pipeline 108 which comprises a plurality of stages for processing an input question and the corpus of data 106. The QA pipeline 108 generates answers for the input question based on the processing of the input question and the corpus of data 106. The QA pipeline 108 will be described in greater detail hereafter with regard to FIG. 3.

In some illustrative embodiments, the cognitive system 100 may be the IBM Watson™ cognitive system available from International Business Machines Corporation of Armonk, N.Y. which is augmented with the mechanisms of the illustrative embodiments described hereafter. As outlined previously, a QA pipeline of the IBM Watson™ cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The QA pipeline of the IBM Watson™ cognitive system then performs deep analysis on the language of the input question and the language used in each of the portions of the corpus of data found during the application of the queries using a variety of reasoning algorithms.

The scores obtained from the various reasoning algorithms are then weighted against a statistical model that summarizes a level of confidence that the QA pipeline of the IBM Watson™ cognitive system has regarding the evidence that the potential response, i.e. candidate answer, is inferred by the question. This process may be repeated for each of the candidate answers to generate ranked listing of candidate answers which may then be presented to the user that submitted the input question, or from which a final answer is selected and presented to the user. More information about the QA pipeline of the IBM Watson™ cognitive system may be obtained, for example, from the IBM Corporation website, IBM Redbooks, and the like. For example, information about the QA pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment recommendation system that analyzes a patient's EMR in relation to medical guidelines and other medical documentation in a corpus of information, to generate a recommendation as to how to treat a medical condition o of the patient. In particular, the cognitive system 100 implements a medical condition independent treatment recommendation (MCITR) system in accordance with one or more of the illustrative embodiments described herein.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a MCITR system 120. It should be appreciated that while the MCIRT system 120 is shown in FIG. 1 as a separate entity from that of the cognitive system 100, the illustrative embodiments are not limited to such. Rather, the elements of the MCITR system 120 may be integrated into the cognitive system 100 and various elements or logic of the MCITR system 120 may be integrated in, or otherwise operate in conjunction with, various logic stages of the request processing pipeline 108. For example, the MCITR system 120 may be implemented as part of, or operate in conjunction with, candidate answer confidences scoring and ranking logic of one or more stages of the request processing pipeline 108.

As shown in FIG. 1, the MCITR system 120 comprises a medical condition cartridge interface 122, a medical condition independent (MCI) scoring feature engine 124, and a MCI score evaluation engine 126, which may include a machine learning model as described herein. It should be appreciated that while these elements 122-126 are specifically shown in FIG. 1, the MCITR system 120 may comprise other elements and logic not specifically shown as separately identified elements in FIG. 1. In general, any functionality or operations described herein that are not specifically attributed to one of the elements 122-126 may be implemented in other logic of the MCITR system 120 including, but not limited to, control logic for controlling the operations of the elements 122-126 and orchestrating their interactions, configuration, and implementation.

The MCITR system 120 is a medical condition independent (MCI) system meaning that it is trained to provide information for generating treatment recommendations where the training is performed in a medical condition independent manner using medical condition independent scoring features. Examples of such medical condition independent (MCI) scoring features include, but are not limited to, a comorbidity score, a patient preference score, an institutional preference score, an inclusion criteria score, an exclusion criteria score, and a drug side effect score. In general, these scores may be provided on a predetermined scoring scale where higher scores indicate a higher presence of the corresponding medical condition independent feature. For example, on a scale of 0 to 100, if a comorbidity score is 75 then this is indicative of a relatively high likelihood of comorbidity sensitivity of a particular medical treatment as opposed to a comorbidity score of 25. Similarly, if a drug side effect score is 10, then the corresponding treatment has a low likelihood of drug side effects as opposed to a score of 90.

The medical condition independent (MCI) scoring features, utilized by the MCI scoring feature engine 124 as described hereafter, aggregate medical condition specific features into an abstracted aggregation of these medical condition specific features in accordance with the specific aggregation logic specified in a medical condition cartridge 130 corresponding to the medical condition. Thus, there may be a large set of possible features that may be aggregated, by the MCI scoring feature engine 124, into a MCI scoring feature of "inclusion feature score", e.g., cancer stage, prior chemotherapy, tumor size, recurrence, etc. and only a subset of those possible features may be specified in the medical condition specific pluggable cartridge 130 for a particular medical condition and treatment as the "inclusion features" to be included when evaluating the patient with regard to whether the particular treatment is appropriate for that medical condition. The MCI scoring features engine 124 merely understands the aggregation of these specified features as an "inclusion feature score" and is not concerned with the way in which this inclusion feature score was generated for a specific treatment for a specific medical condition. To the contrary, the specific way in which the inclusion feature score is generated, and what elements are components of this inclusion feature score, are specified in the medical condition cartridge 130 for the particular medical condition.

As shown in FIG. 1, the MCITR system 120 comprises a medical condition cartridge interface 122 which provides a communication interface and logic for receiving an input of one or more medical condition cartridges 130, ingesting the information present in the one or more medical condition cartridges 130, and customizing the configuration of the medical condition independent (MCI) feature engine 124 for evaluating patients with regard to the specific medical condition(s) associated with the ingested cartridges 130. The MCI scoring feature engine 124 maps patient attributes, treatment attributes, and medical condition attributes to MCI scoring features or otherwise provides configuration information for configuring the manner by which a particular MCI scoring feature is generated based on specific elements of patient attributes, treatment attributes, and medical condition attributes. These MCI scoring features may be provided by the MCI scoring feature engine 124 to a trained MCI score evaluation engine 126 which evaluates the suitableness of a treatment for a particular patient, based on the evaluation of patient specific features via the MCI scoring feature engine 124, to generate MCI scoring features specific to the patient. The MCI score evaluation engine 126 generates a confidence score, or at least one factor for generating a confidence score along with other factors generated based on information gathered from the corpus 132, which is associated with treatments for medical conditions that the patient may have. These confidence scores may be used to rank various treatments for the patient via the cognitive system 100 and request processing pipeline 108. Subsequently, a final treatment recommendation, or ranked set of treatment recommendations, may be returned to an originator of the request/input question, e.g., a user of client device 110.

It should be appreciated that the MCI score evaluation engine 126 implements a medical condition independent model for evaluating medical condition independent scoring features. Thus, for example, the MCI score evaluation engine 126 may indicate that a particular combination of weights associated with an inclusion scoring feature, exclusion scoring feature, comorbidity scoring feature, and the like, are to be used and a particular function is to be used to combine these scoring features to generate a confidence score, or confidence score factor to be included with other confidence score factors, for a treatment. It should be appreciated that the MCI score evaluation engine 126 may be general such that the same weights and combination logic/functions may be used to generate confidence scores for a plurality of different medical conditions, treatments, and patient attributes such that the MCI score evaluation engine 126 is medical condition independent or agnostic.

In some illustrative embodiments, the MCI score evaluation engine 126 may be general with regard to a particular class or domain of medical conditions, e.g., cancers as one class, blood diseases as another class, liver function diseases as another class, etc. Within each class there may be multiple different specific medical conditions that may be specified in medical condition cartridges 130. Thus, there may be multiple different MCI score evaluation engine instances 126 for different classes or domains of medical conditions which are still medical condition independent or agnostic but are specifically trained for a particular class or domain of medical conditions.

Such training may be performed in any known or later developed manner using information from the corpus 132, which may include training data sets representing patients, medical knowledge and guidelines, actual medical conditions, and correct treatments for such medical conditions as determined by subject matter experts or medical personnel. The training is done with regard to medical condition independent (MCI) scoring features that are independent of the particular medical conditions of the individual patients specified in the training data sets. The training causes specific weights and logic for combining the MCI scoring features to be generated for the specific class or domain of medical conditions, or medical conditions in general.

Once trained in this manner, during runtime operation, the MCITR system 120 utilizes the trained MCI score evaluation engine 126 to apply the trained model of weights and logic to particular MCI scoring features generated for a particular patient with regard to a particular medical condition and treatment as specified in a medical condition cartridge 130 using the mapping performed by the MCI scoring feature engine 124. That is, the medical condition cartridge 130 specifies that for a particular medical condition, e.g., type 2 diabetes, there are a plurality of different treatments, with each treatment having its own combination of patient attributes, treatment attributes, and medical condition attributes that are mapped to different MCI scoring features in a particular manner (e.g., particular weights associated with different attributes, different combination logic for different attributes, etc.). This information is used to configure the MCI scoring feature engine 124 to map patient specific attributes, treatment attributes, and medical condition attributes based medical condition specific scores as indicated by application of specified in the medical condition cartridge 130 to MCI score features. A particular patient's information is input to the MCITR system 120 which then evaluates the particular patient's information with regard to various medical conditions and treatments via the MCI scoring feature engine 124 to generate patient specific MCI scoring features for each combination of medical condition/treatment specified in the ingested medical condition cartridge(s) 130. These patient specific MCI scoring features may then be input to the MCI score evaluation engine 126. The MCI score evaluation engine 126 generates a confidence score for each combination of medical condition/treatment for this patient and provides the confidence score back to the cognitive system 100. The confidence score may be used, either alone or in combination with other confidence score factors such as may be obtained from evaluation of the evidence in the corpus 132, to generate a ranked listing of treatments for medical conditions of the patient. This ranked listing is used to generate a final treatment recommendation or final set of ranked treatment recommendations to be returned to the requestor, potentially categorized into different levels of treatment recommendation as mentioned previously.

FIG. 2 is a block diagram of an example data processing system in which aspects of the illustrative embodiments are implemented. Data processing system 200 is an example of a computer, such as computing devices 104 or client 110 in FIG. 1, in which computer usable code or instructions implementing the processes for illustrative embodiments of the present invention are located. In one illustrative embodiment, FIG. 2 represents a server computing device, such as a computing devices 104, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical condition or condition to a user 306, such as a healthcare practitioner, technician, or the like. The user 306 may interact with the patient 302 via a question 314 and response 316 exchange where the user gathers more information about the patient 302, the symptoms 304, and the medical condition or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical condition/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);
Patient has AML=AML (MET); and
Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refuting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to operate with, implement, or include a medical condition independent treatment recommendation system 340, such as MCITR system 120 in FIG. 1. While the above description describes a general healthcare cognitive system 300 that may operate on specifically configured treatment recommendation rules, the mechanisms of the illustrative embodiments modify such operations to utilize the MCITR system 340 which is medical condition independent or agnostic and operates in the manner previously described above with regard to FIG. 1.

Thus, in response to the healthcare cognitive system 300 receiving the request 308 and patient attributes 318, the healthcare cognitive system 300 may retrieve the patient's EMR data from source(s) 322. This information is provided to MCITR system 340 which is configured with medical condition (MC) specific cartridges 350 for one or more medical conditions and corresponding treatments for which the patient is to be evaluated. In some illustrative embodiments, the request 308 may specify the types of medical conditions, class or classes of medical conditions, or domain(s) of medical conditions to be considered with regard to the specified patient, e.g., "what treatment should I prescribe to patient A for her diabetes?" indicates that the medical condition or medical class/domain is diabetes. If such specification is made in the request 308, then the corresponding MC cartridges 350 may be loaded or ingested so as to configure the MCITR system 340 operation for class(es) or domain(s) of the medical conditions corresponding to the specific request 308.

The patient attributes 318 and patient EMR information from source(s) 322 are input to the MCITR system 340 configured with the corresponding MC cartridges 350 which causes the patient attributes 318 and patient EMR information to be analyzed and combined into MCI scoring features which are then evaluated by the MCI score evaluation logic of the MCITR system 340 in accordance with its medical condition independent or agnostic training. The result is a confidence score, or at least a confidence score factor, for each potential treatment recommendation which is output to the healthcare cognitive system 300 and used as part of its evaluation of potential treatments for the patient specified in the request 308. The healthcare cognitive system 300 may evaluate these confidence scores of treatment recommendations along with other information in the medical corpus and other source data 326 and treatment guidance data 324 to generate final confidence scores for various treatment recommendations. The final confidence scores may then be ranked by the healthcare cognitive system 300 relative to one another and used to generate a final treatment recommendation 328, or categorized set of treatment recommendations.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention.

As mentioned above, the healthcare cognitive system 300 may include a request processing pipeline, such as request processing pipeline 108 in FIG. 1, which may be implemented, in some illustrative embodiments, as a Question Answering (QA) pipeline. The QA pipeline may receive an input question, such as "what is the appropriate treatment for patient P?", or a request, such as "diagnose and provide a treatment recommendation for patient P."

Figure 4:
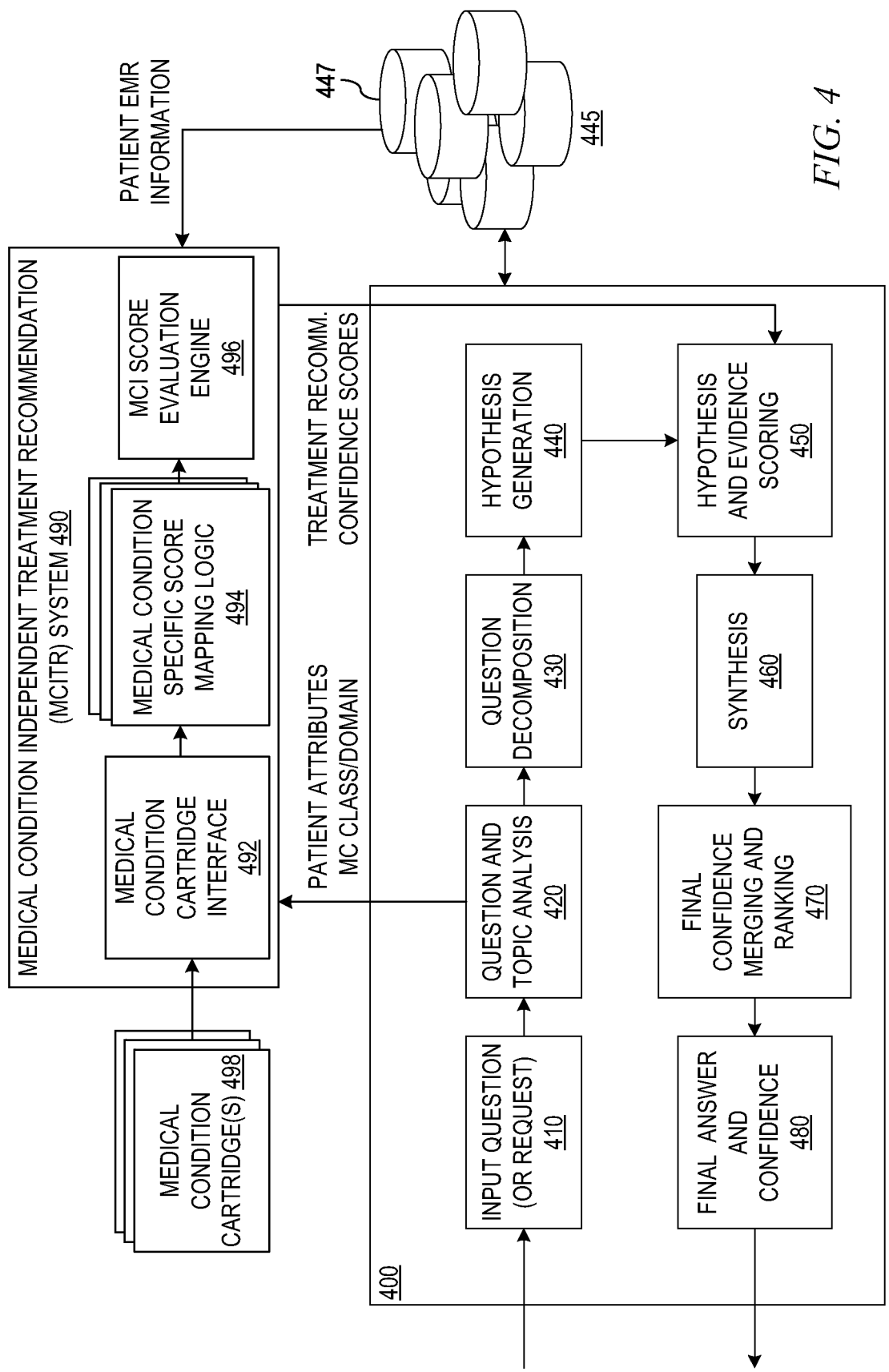
FIG. 4 illustrates a cognitive healthcare system implementing a Question and Answer (QA) or request processing pipeline for processing an input question or request in accordance with one illustrative embodiment.

FIG. 4 illustrates a QA pipeline of a healthcare cognitive system, such as healthcare cognitive system 300 in FIG. 3, or an implementation of cognitive system 100 in FIG. 1, for processing an input question in accordance with one illustrative embodiment. It should be appreciated that the stages of the QA pipeline shown in FIG. 4 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The QA pipeline of FIG. 4 is augmented, for example, in one or more of the stages to implement the improved mechanism of the illustrative embodiments described hereafter, additional stages may be provided to implement the improved mechanism, or separate logic from the pipeline 400 may be provided for interfacing with the pipeline 400 and implementing the improved functionality and operations of the illustrative embodiments.

As shown in FIG. 4, the QA pipeline 400 comprises a plurality of stages 410-480 through which the cognitive system operates to analyze an input question and generate a final response. In an initial question input stage 410, the QA pipeline 400 receives an input question that is presented in a natural language format. That is, a user inputs, via a user interface, an input question for which the user wishes to obtain an answer, e.g., "What medical treatments for diabetes are applicable to a 60 year old patient with cardiac disease?" In response to receiving the input question, the next stage of the QA pipeline 400, i.e. the question and topic analysis stage 420, parses the input question using natural language processing (NLP) techniques to extract major features from the input question, and classify the major features according to types, e.g., names, dates, or any of a plethora of other defined topics. For example, in a question of the type "Who were Washington's closest advisors?", the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic. Similarly, in the previous question "medical treatments" may be associated with pharmaceuticals, medical procedures, holistic treatments, or the like, "diabetes" identifies a particular medical condition, "60 years old" indicates an age of the patient, and "cardiac disease" indicates an existing medical condition of the patient.

In addition, the extracted major features include key words and phrases, classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of ADD with relatively few side effects?," the focus is "drug" since if this word were replaced with the answer, e.g., the answer "Adderall" can be used to replace the term "drug" to generate the sentence "Adderall has been shown to relieve the symptoms of ADD with relatively few side effects." The focus often, but not always, contains the LAT. On the other hand, in many cases it is not possible to infer a meaningful LAT from the focus.

Referring again to FIG. 4, the identified major features are then used during the question decomposition stage 430 to decompose the question into one or more queries that are applied to the corpora of data/information 445 in order to generate one or more hypotheses. The queries are generated in any known or later developed query language, such as the Structure Query Language (SQL), or the like. The queries are applied to one or more databases storing information about the electronic texts, documents, articles, websites, and the like, that make up the corpora of data/information 445. That is, these various sources themselves, different collections of sources, and the like, represent a different corpus 447 within the corpora 445. There may be different corpora 445 defined for different collections of documents based on various criteria depending upon the particular implementation. For example, different corpora may be established for different topics, subject matter categories, sources of information, or the like. As one example, a first corpus may be associated with healthcare documents while a second corpus may be associated with financial documents. Alternatively, one corpus may be documents published by the U.S. Department of Energy while another corpus may be IBM Redbooks documents. Any collection of content having some similar attribute may be considered to be a corpus 447 within the corpora 445.

The queries are applied to one or more databases storing information about the electronic texts, documents, articles, websites, and the like, that make up the corpus of data/information, e.g., the corpus of data 106 in FIG. 1. The queries are applied to the corpus of data/information at the hypothesis generation stage 440 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 440, to generate hypotheses for answering the input question. These hypotheses are also referred to herein as "candidate answers" for the input question. For any input question, at this stage 440, there may be hundreds of hypotheses or candidate answers generated that may need to be evaluated.

The QA pipeline 400, in stage 450, then performs a deep analysis and comparison of the language of the input question and the language of each hypothesis or "candidate answer," as well as performs evidence scoring to evaluate the likelihood that the particular hypothesis is a correct answer for the input question. As mentioned above, this involves using a plurality of reasoning algorithms, each performing a separate type of analysis of the language of the input question and/or content of the corpus that provides evidence in support of, or not in support of, the hypothesis. Each reasoning algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In generally, however, these algorithms look for particular terms, phrases, or patterns of text that are indicative of terms, phrases, or patterns of interest and determine a degree of matching with higher degrees of matching being given relatively higher scores than lower degrees of matching.

Thus, for example, an algorithm may be configured to look for the exact term from an input question or synonyms to that term in the input question, e.g., the exact term or synonyms for the term "movie," and generate a score based on a frequency of use of these exact terms or synonyms. In such a case, exact matches will be given the highest scores, while synonyms may be given lower scores based on a relative ranking of the synonyms as may be specified by a subject matter expert (person with knowledge of the particular domain and terminology used) or automatically determined from frequency of use of the synonym in the corpus corresponding to the domain. Thus, for example, an exact match of the term "movie" in content of the corpus (also referred to as evidence, or evidence passages) is given a highest score. A synonym of movie, such as "motion picture" may be given a lower score but still higher than a synonym of the type "film" or "moving picture show." Instances of the exact matches and synonyms for each evidence passage may be compiled and used in a quantitative function to generate a score for the degree of matching of the evidence passage to the input question.

Thus, for example, a hypothesis or candidate answer to the input question of "What was the first movie?" is "The Horse in Motion." If the evidence passage contains the statements "The first motion picture ever made was 'The Horse in Motion' in 1878 by Eadweard Muybridge. It was a movie of a horse running," and the algorithm is looking for exact matches or synonyms to the focus of the input question, i.e. "movie," then an exact match of "movie" is found in the second sentence of the evidence passage and a highly scored synonym to "movie," i.e. "motion picture," is found in the first sentence of the evidence passage. This may be combined with further analysis of the evidence passage to identify that the text of the candidate answer is present in the evidence passage as well, i.e. "The Horse in Motion." These factors may be combined to give this evidence passage a relatively high score as supporting evidence for the candidate answer "The Horse in Motion" being a correct answer.

It should be appreciated that this is just one simple example of how scoring can be performed. Many other algorithms of various complexity may be used to generate scores for candidate answers and evidence without departing from the spirit and scope of the present invention.

In the synthesis stage 460, the large number of scores generated by the various reasoning algorithms are synthesized into confidence scores or confidence measures for the various hypotheses. This process involves applying weights to the various scores, where the weights have been determined through training of the statistical model employed by the QA pipeline 400 and/or dynamically updated. For example, the weights for scores generated by algorithms that identify exactly matching terms and synonym may be set relatively higher than other algorithms that are evaluating publication dates for evidence passages. The weights themselves may be specified by subject matter experts or learned through machine learning processes that evaluate the significance of characteristics evidence passages and their relative importance to overall candidate answer generation.

The weighted scores are processed in accordance with a statistical model generated through training of the QA pipeline 400 that identifies a manner by which these scores may be combined to generate a confidence score or measure for the individual hypotheses or candidate answers. This confidence score or measure summarizes the level of confidence that the QA pipeline 400 has about the evidence that the candidate answer is inferred by the input question, i.e. that the candidate answer is the correct answer for the input question.

The resulting confidence scores or measures are processed by a final confidence merging and ranking stage 470 which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/ candidate answers (hereafter simply referred to as "candidate answers"). From the ranked listing of candidate answers, at stage 480, a final answer and confidence score, or final set of candidate answers and confidence scores, are generated and output to the submitter of the original input question via a graphical user interface or other mechanism for outputting information.

As shown in FIG. 4, in accordance with one illustrative embodiment, the QA pipeline 400 is augmented to work in conjunction with the MCITR system 490. As noted above, rather than the MCITR system 490 being a separate entity as shown, elements of the MCITR system 490 may be integrated into the logic of one or more of the stages 410-480 of the QA pipeline 400. The QA pipeline 400 may provide patient attributes and optionally an indication of the medical condition (MC) class(es)/domain(s) with which the input question 410 is associated, such as may be identified from analysis of the input question 410 in stage 420.

The MCITR system 490 is preferably previously trained in a medical condition independent or agnostic manner to provide MCI score evaluation engine 496 which operates on medical condition independent (MCI) scoring features to generate a confidence score for treatment recommendations. The MCITR system 490, optionally based on a MC class/ domain identified for the input question 410 as communicated by stage 420 to the MCITR system 490, loads or ingests a medical condition cartridge 498 in a pluggable manner such that the particular patient features, treatment features, and medical condition features specific to the particular medical condition, and the particular logic used to combine these features to map to particular MCI scoring features are ingested by the MCITR system 490 via interface 492. More than one cartridge 498 may be loaded/ingested in this manner to generate one or more medical condition specific score mapping logic elements 494.

Patient attribute information received from the QA pipeline 400 as part of the input question, as well as the EMRs for the identified patient, may be input to the MCITR system 490 which then applies the specific values specified in the EMRs and patient attribute information to the particular medical condition specific features to generate patient specific MCI scoring feature values, e.g., the patients' age, gender, race, etc., may be combined in a manner specifically set forth in the loaded/ingested MC cartridge 498 to generate a particular value for a MCI scoring feature of "inclusion feature score" and/or "exclusion feature score". For example, based on the medical condition cartridge 498, it may be determined that patients that are less than 60 years old can receive a corresponding treatment for the medical condition and thus, for an "inclusion feature score" if the patient is less than 60 years old, a value of "1" may be provided, while in the "exclusion feature score" this may result in a value of "0" indicating that the patient is not excluded from the treatment. Similarly, if the patient is 60 years old or older, the values would be reversed such that the inclusion feature score would be "0" and the exclusion feature score would be "1". Different weights may be assigned to different features as part of the aggregation functions or logic that aggregates these medical condition specific features into MCI scoring features.

The generated MCI scoring features are then input to a corresponding MCI score evaluation engine 496. There may be multiple different MCI score evaluation engines 496 configured to operate on different classes or domains of medical conditions in some illustrative embodiments and thus, based on the identified MC class/domain in the input from the QA pipeline 400, the MCITR system 490 may determine which MCI score evaluation engine 496 applies to the particular class/domain of the medical condition or conditions specified in the input question or request 410.

The corresponding MCI score evaluation engine 496 generates, for each possible treatment recommendation for each of the medical conditions in the medical condition cartridge(s) 498 loaded by the MCITR system 490 for use with the input question or request 410, a treatment recommendation confidence score based on a trained model for combining the MCI scoring features. The resulting treatment recommendation confidence scores are sent back to the QA pipeline 400, such as to the logic of the hypothesis and evidence scoring stage 450. The logic of stage 450 may then utilize these confidence scores as the final confidence scores for the corresponding treatment recommendations or may combine these confidence scores with other evaluation factors considered by the hypothesis and evidence scoring logic 450 including evaluation of evidential passages from the corpus 44 or corpora 445. The results generated by logic 450 are then synthesized in stage 460 and final confidence merging and ranking 470 as well as final answer and confidence output generation 480 are performed in the manner previously described above. Thus, a treatment recommendation, or set of ranked treatment recommendations with corresponding confidence scores and possibly supporting evidence passages and the like, may be generated for an input question or request 410 using a medical condition independently trained treatment recommendation system.

Figure 5:
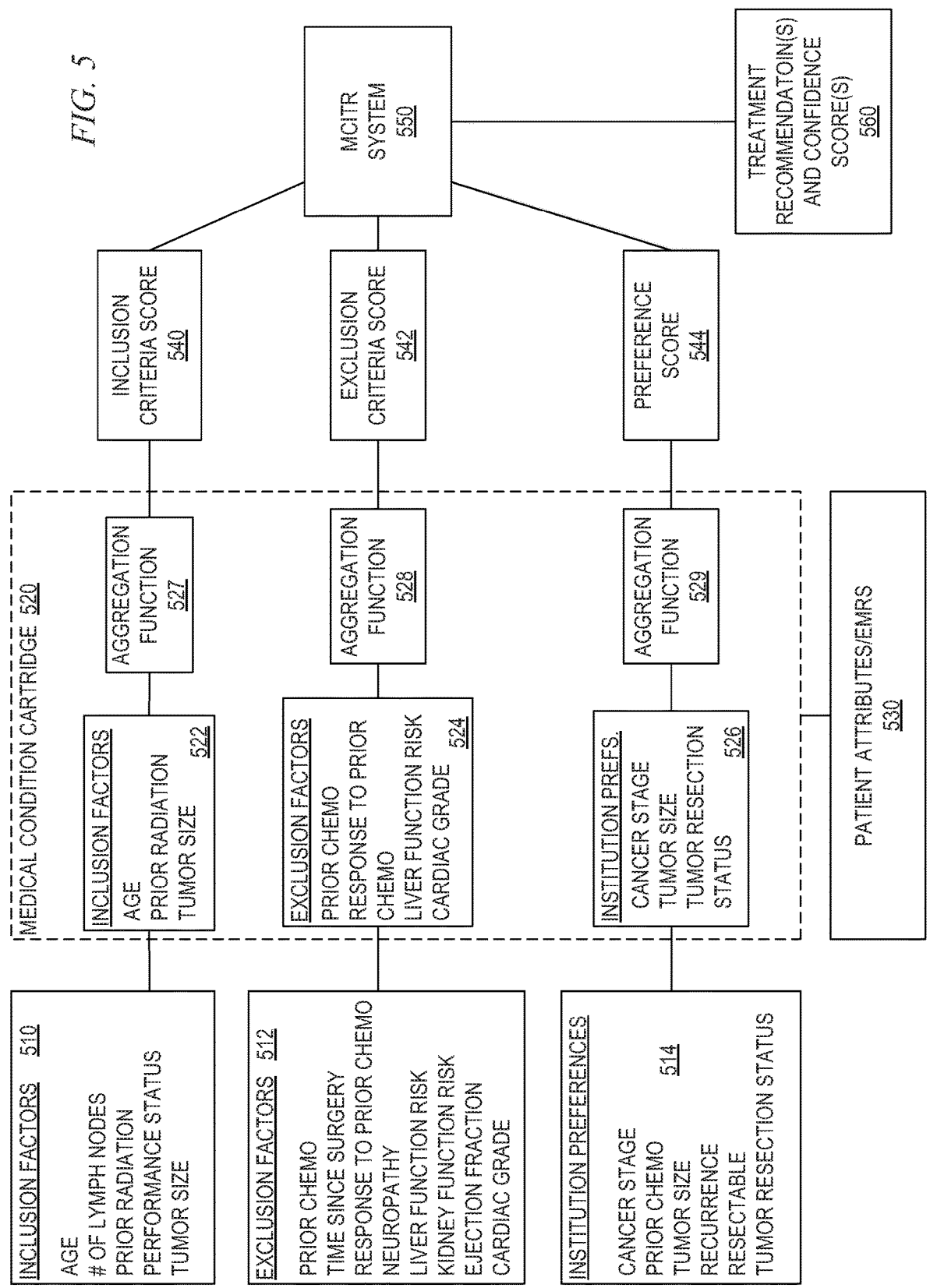
FIG. 5 is a flowchart outlining an example operation for configuring a treatment recommendation system implementing a medical condition independent engine for use with specific medical conditions provided in a pluggable cartridge manner in accordance with one illustrative embodiment.

FIG. 5 is an example diagram illustrating an example interaction between a medical condition specific cartridge, patient attributes and EMR information, and the medical condition independent score evaluation engine in accordance with one illustrative embodiment. As shown in FIG. 5, there is a large set of potential factors 510, 512, and 514 that may be considered when determining the applicability of a particular treatment for a particular medical condition. These potential factors may be generally associated with different types of factors such as inclusion factors, exclusion factors, institution preferences, comorbidity factors, patient preferences, drug side effect factors, and the like. In the depicted example, the potential factors are categorized into inclusion factors 510 which are indicative of factors that tend to indicate the appropriateness of a treatment for a particular patient to treat a particular medical condition, exclusion factors 512 that indicate factors tending to indicate the inappropriateness of a treatment for a particular patient to treat a particular medical condition, and institution preferences 514 which indicate factors that an institution deems important for recommending a particular treatment for a particular patient to treat a particular medical condition. Each of these categories of factors 510, 512, and 514 may have one or more individual factors that fall within the categories. For example, in the depiction, the individual factors of age, number of lymph nodes, prior radiation, tumor size, etc. are categorized as inclusion factors. It should be appreciated that the same factor may be categorized in different categories 510, 512, and 514 depending on the particular implementation.

The medical condition cartridge 520 provides subsets of these factors in the various groupings 510, 512, and 514 that are pertinent to treatments for the particular medical condition represented by the cartridge 520. Thus, for one medical condition and treatment combination, age may be a factor whereas for a different medical condition and treatment combination, age may not be a factor. The medical condition cartridge 520 specifies the particular subsets 522-526 of these factors that are pertinent for each treatment recommendation specified in the medical condition cartridge 520. Thus, a medical condition cartridge 520 may have multiple candidate treatments indicated for the same medical condition. Each of these candidate treatments may have their own subsets of factors that are pertinent to the appropriateness or efficacy of that treatment for a particular set of patient attributes when treating the medical condition. For purposes of ease of illustration, medical condition cartridge 520 assumes a single treatment being specified for the medical condition in the medical condition cartridge 520, however it should be appreciated that the elements shown in the medical condition cartridge 520 may be replicated and customized for a plurality of different treatments for the same medical condition associated with the medical condition cartridge 520. Alternatively, separate cartridges 520 may be provided for separate combinations of medical condition and treatment, depending on the desired implementation.

Moreover, the medical condition cartridge 520 further specifies, for each treatment recommendation, corresponding mapping functions 527-529 for mapping factors to medical condition independent (MCI) scoring features 540-544 which aggregate the medical condition specific scoring features or factors to medical condition independent scoring features or factors. The mapping functions 527-529 operate on the subset of the corresponding type of factors to aggregate this subset of factors to generate a corresponding MCI scoring feature 540-544. Thus, for example, the subset of inclusion factors 522 specified in the medical condition cartridge 520 for the specific medical condition and corresponding candidate treatment are aggregated in accordance with the mapping function 527 to generate a MCI scoring feature of "inclusion criteria score" 540. Similarly, the subset 524 of exclusion factors are aggregated using mapping function 528 to generate "exclusion criteria score" MCI scoring feature 542.

The patient information and EMRs 530 are input to the system and used to provide actual values for the various factors in the subset of factors 522-526. This gives rise to specific values or scores for the various MCI scoring features 540-544.

The MCI scoring features 540-544 are input to the MCITR system 550 which has been trained, such as via one or more machine learning techniques, either known or later developed, in a medical condition independent or agnostic manner. For example, this training may include using a ground truth or golden set of data that indicates a correct output of the MCITR system 550 for particular inputs. The parameters, e.g., weights, particular functions, and the like, utilized by the MCITR system 550 when evaluating the various aggregated MCI scoring features 540-544 to rank treatment recommendations for medical conditions in general, may be adjusted through an iterative process to make the output of the MCITR system 550 approach the correct output as indicated by the ground truth or golden set of data. It should be appreciated that this training is performed with regard to the MCI scoring features and is not specific to any particular medical condition or particular treatment for a medical condition. In some illustrative embodiments, while the training may involve specific medical conditions and treatments for purposes of training the MCITR system 550 with regard to MCI scoring features, the resulting trained model of the MCITR system 550 is medical condition independent or agnostic, e.g., the training may utilize data corresponding to various medical conditions including diabetes, cancers, and the like, the training results in MCI scoring feature based weights and parameters that are utilized in a medical condition independent or agnostic manner.

Thus, the MCITR system 550 operates specifically on the MCI scoring features 540-544 and is not dependent on particular factors 510-514 or particular subsets of factors 522-526 for any particular medical condition. Thus, the MCITR system 550 provides a pluggable framework that is trained to provide medical condition and treatment independent or agnostic evaluations of aggregate scoring features. This pluggable framework may be specifically configured for particular medical conditions and their corresponding candidate treatments by way of plugging in the desired medical condition cartridges 520 corresponding to those medical conditions and treatments that are to be evaluated. Thus, the generic framework is specifically configured for particular medical conditions/treatments without having to train the model used by the generic framework for each possible combination of medical condition and candidate treatment.

As mentioned above, the MCITR system 550 operates on the particular MCI scoring feature values 540-544 to generate confidence scores for the various treatments specified in the medical condition cartridge 520. These confidence scores 560 are output to the QA pipeline for further evidence scoring, if desired by the particular implementation, and ranking of candidate treatments and final selection of one or more candidate treatments as a treatment recommendation for the original input question or request.

Figure 6:
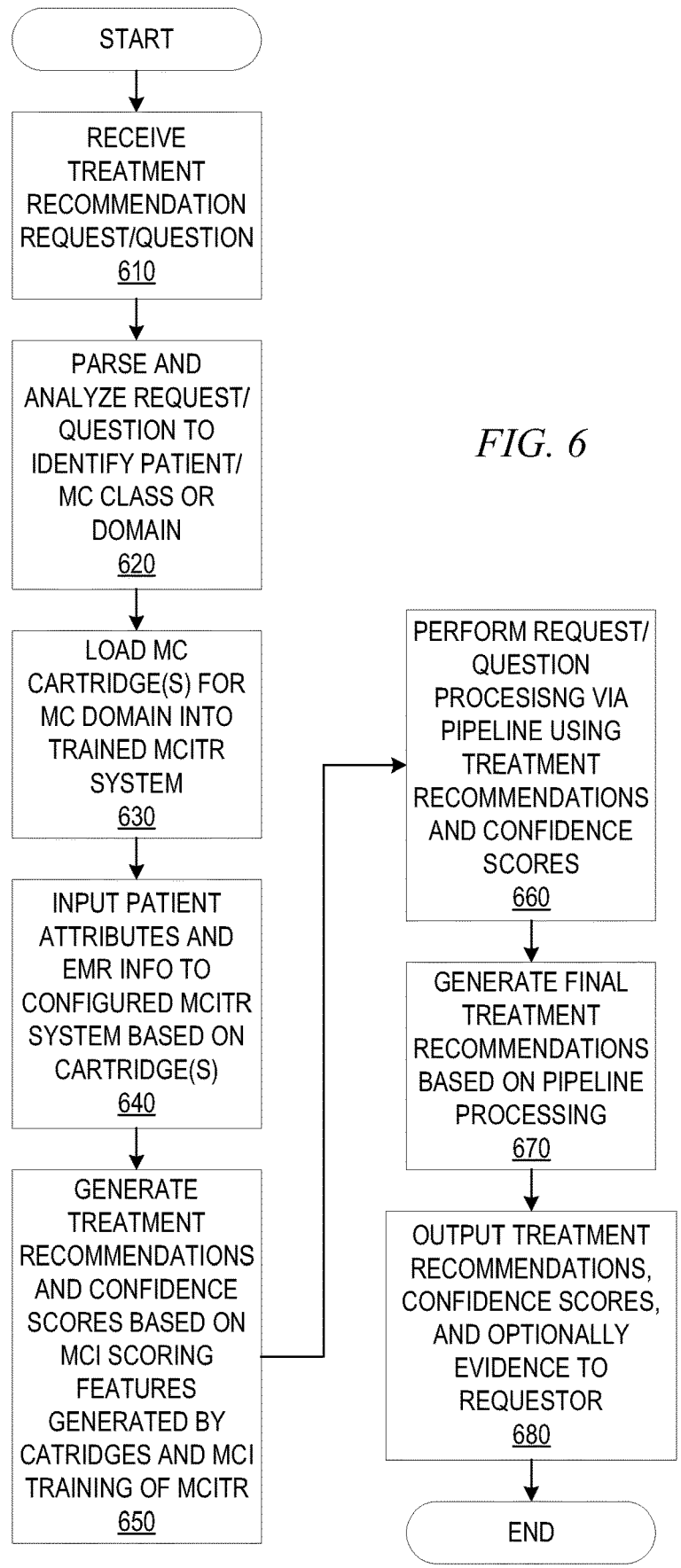
FIG. 6 is a flowchart outlining an example operation for generating a medical treatment recommendation for treating a patient using a medical condition independent engine and pluggable cartridge in accordance with one illustrative embodiment.

FIG. 6 is a flowchart outlining an example operation for processing a medical treatment input question or request for a patient utilizing a MCITR system in accordance with one illustrative embodiment. The operation shown in FIG. 6 assumes that the MCITR system has already been trained in a medical condition independent or agnostic manner based on the medical condition independent scoring features, as previously described above. Thus, the MCITR is not specific to any particular medical condition or treatments but can be used to evaluate various treatments for various medical conditions based on specific configurations identified in medical condition cartridges that are pluggable into the MCITR system framework. That is, the medical condition specific cartridges provide medical condition and associated treatment recommendation specific configurations for mapping various factors, e.g., patient attributes, EMR information, treatment attributes, medical condition attributes, and the like, to functions for generating a medical condition independent scoring feature for that particular combination of medical condition and treatment.

As shown in FIG. 6, the operation starts with receiving a treatment recommendation request/question (step 610). The request/question is then parsed and analyzed to identify the particular patient and the medical condition class or domain for which the patient is to be evaluated (step 620). It should be appreciated that this request/question may be manually generated and/or automatically generated. For example, a medical professional (user) may initiate a request manually through a user interface requesting that the system provide the medical professional a recommended treatment for treating a patient, Sally Jones, for the user specified medical condition of type 2 diabetes, e.g., "Provide treatment recommendations for Sally Jones' type 2 diabetes." Alternatively, the medical professional may provide a question of the type "What treatments are recommended for Sally Jones" and the system may evaluate Sally Jones' EMR to determine her medical condition and then configure the MCITR system for that particular medical condition in an automated manner. Any manual, automated, or semi-automated manner for generating the request/question may be used without departing from the spirit and scope of the present invention.

Continuing with the operation outlined in FIG. 6, the medical condition (MC) specific cartridge(s) that correspond to the identified MC class or domain are loaded, such as in a pluggable manner, into the trained MCITR system to thereby configure the MCITR system to evaluate the patient with regard to these medical conditions (step 630). The patient attributes and EMR information for the identified patient is input to the configured MCITR system which has been configured based on the MC cartridge(s) (step 640).

The MCITR operates on the patient attributes and EMR information to generate confidence scores for treatment recommendations specified in the MC cartridges based on the generation of MCI scoring features in the manner specifically identified in the MC cartridges for each combination of medical condition and treatment recommendation specified in the MC cartridges, and further based on the MCI training of the MCITR system (step 650). The treatment recommendations and confidence scores are input to the question/request processing pipeline which performs its cognitive analysis and processing of these treatment recommendations and confidence scores (step 660). This processing may involve further evidential support analysis based on a corpus or corpora of information to find evidence that supports/refutes the treatment recommendations and combines the evaluation of such evidence with the confidence scores associated with the treatment recommendations as generated by the MCITR system. The question/request processing pipeline generates one or more final treatment recommendations (step 670) and outputs those final treatment recommendations, confidence scores, and optionally evidence to the originator of the request/question (step 680). The operation then terminates.

Thus, the illustrative embodiments provide mechanisms for implementing a medical condition independent or agnostic treatment recommendation system that is trained using a relatively small set of features or factors that are not medical condition specific. All of the medical condition specific logic is moved out of the feature set used to train the system and instead is provided in medical condition specific cartridges. These cartridges are provided in a pluggable manner such that they may be utilized to customize the operation of the system to particular medical conditions. Such customization may be done on a dynamic basis based on the particular classes or domains of medical conditions for which a patient is being considered. In this way, the system may be trained more easily and with less outlay of resources, especially with regard to training data sets.

As discussed above, in one illustrative embodiment, mechanisms are provided to implement a medical treatment recommendation system. The mechanisms configure a medical treatment recommendation system to implement a medical condition independent treatment recommendation model. The medical condition independent treatment recommendation model is trained on, and operates on, medical condition independent scoring features that are independent of any specific medical condition. The mechanisms configure the medical treatment recommendation system to receive a medical condition cartridge that provides medical condition specific scoring logic that is specific to a particular medical condition. Moreover, the mechanisms process patient information for a patient based on a combination of an execution of the medical condition specific scoring logic associated with the medical condition cartridge, and an execution of the medical condition independent treatment recommendation model of the medical treatment recommendation system, to generate at least one treatment recommendation for a patient medical condition associated with the patient. In addition, the mechanisms output the at least one treatment recommendation for the patient.

In some optional illustrative embodiments, the medical condition specific scoring logic generates, for the particular medical condition, at least one medical condition independent scoring feature of the medical condition independent scoring features of the medical condition independent treatment recommendation model in a manner that is specific to the particular medical condition. Moreover, in other optional illustrative embodiments the medical condition cartridge receives patient information as input and the medical condition specific scoring logic evaluates factors in the patient information to generate the at least one medical condition independent scoring feature in a manner specific to a combination of the specific medical condition and a candidate treatment. Optionally, the factors may comprise one or more factors selected from the set comprising patient factors defining characteristics of the patient and medical condition factors defining characteristics of the patient medical condition.

In some optional illustrative embodiments, processing patient information for the patient comprises: receiving, by the medical treatment recommendation system, an electronic medical record (EMR) of the patient comprising patient factors representing a medical state of the patient; executing, by the medical treatment recommendation system, the medical condition specific scoring logic of the medical condition cartridge to generate a medical condition independent scoring feature for a combination of the specific medical condition, a candidate treatment, and the patient factors of the patient, based on an aggregation function specified in the medical condition cartridge; and applying, by the medical treatment recommendation system, the medical condition independent treatment recommendation model to the medical condition independent scoring feature to generate a candidate treatment recommendation confidence score for the candidate treatment.

In still other optional illustrative embodiments, processing the patient information comprises executing the medical condition specific scoring logic of the medical condition cartridge to: perform calculations that are specific to the particular medical condition and a particular candidate treatment, to generate medical condition specific score values; and apply one or more aggregation operations to one or more subsets of the medical condition specific score values to generate aggregation values, each aggregation value corresponding to one of the medical condition independent scoring features of the medical condition independent treatment recommendation model. In some optional illustrative embodiments, the medical condition cartridge comprises multiple different instances of medical condition specific scoring logic, each instance being associated with the particular medical condition but being further associated with a different candidate treatment for the particular medical condition.

In still further optional illustrative embodiments, the calculations operate on patient factors that provide characteristics of the patient, medical condition factors that characterize the particular medical condition, and candidate treatment factors characterizing aspects of the candidate treatment. Moreover, in some optional illustrative embodiments, the calculations operate to evaluate patient specific characteristics, obtained from an electronic medical record associated with the patient, with regard to weighted variables in the medical condition specific scoring logic. Furthermore, in some optional illustrative embodiments, each aggregation operation of the one or more aggregation operations map an aggregate value of a subset of the medical condition specific score values to a corresponding medical condition independent scoring feature. In some illustrative embodiments, at least two aggregation operations in the one or more aggregation operations operate on a different subset of the medical condition specific score values.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, wherein the at least one memory comprises instructions which are executed by the at least one processor to specifically configure the data processing system to implement a medical treatment recommendation system, the method comprising:

configuring, by a medical condition independent score evaluation engine of the medical treatment recommendation system, a medical condition independent treatment recommendation model, wherein the medical condition independent treatment recommendation model is trained on, and operates on, a set of medical condition independent scoring features that are independent of any specific medical condition, wherein the set of medical condition independent scoring features comprise an inclusion criteria score feature, an exclusion criteria score feature, and a preference score feature;

loading, by a medical condition cartridge interface of the medical treatment recommendation system, a pluggable medical condition cartridge into a cognitive system to be utilized in a machine learning process to provide a set of medical condition specific evaluation features that are specific to a particular medical condition, wherein the machine learning process that provides the set of medical condition specific evaluation features that are specific to the particular medical condition is trained by:
   adjusting one or more parameters utilized to evaluate an aggregate of the inclusion criteria score feature, the exclusion criteria score feature, and the preference score feature so as to provide an output as indicated by either a ground truth or golden set of data that not specific to any particular medical condition or particular treatment for a medical condition;

mapping, by a medical condition independent score feature engine of the medical treatment recommendation system, each of the set of medical condition specific evaluation features to a medical condition independent scoring feature in the set of medical condition independent scoring features;

processing, by the medical condition independent score evaluation engine, patient information for a patient based on application of the mapping of the set of medical condition specific evaluation features, associated with the pluggable medical condition cartridge, and the medical condition independent treatment recommendation model of the medical treatment recommendation system, to generate at least one treatment recommendation for a patient medical condition associated with the patient; and outputting, by the data processing system to a client device, the at least one treatment recommendation for the patient.

2. The method of claim 1, further comprising:
generating, for the particular medical condition, at least one medical condition independent scoring feature, of the set of medical condition independent scoring features of the medical condition independent treatment recommendation model, in a manner that is specific to the particular medical condition.

3. The method of claim 1, further comprising:
generating at least one medical condition independent scoring feature, of the set of medical condition independent scoring features of the medical condition independent treatment recommendation model, in a manner specific to a combination of the particular medical condition and a candidate treatment.

4. The method of claim 3, wherein the factors comprise one or more factors selected from the set comprising patient factors defining characteristics of the patient and medical condition factors defining characteristics of the patient medical condition.

5. The method of claim 1, wherein processing patient information for the patient comprises:
receiving, by the medical treatment recommendation system, an electronic medical record (EMR) of the patient comprising patient factors representing a medical state of the patient;
executing, by the medical treatment recommendation system, logic that applies at least one of the set of medical condition specific evaluation features of the pluggable medical condition cartridge to generate at least one medical condition independent scoring feature, of the set of medical condition independent scoring features of the medical condition independent treatment recommendation model, for a combination of the specific medical condition, a candidate treatment, and the patient factors of the patient, based on an aggregation function specified in the pluggable medical condition cartridge; and
applying, by the medical treatment recommendation system, the medical condition independent treatment recommendation model to the at least one medical condition independent scoring feature to generate a candidate treatment recommendation confidence score for the candidate treatment.

6. The method of claim 1, wherein processing the patient information comprises executing logic that applies the set of medical condition specific evaluation features of the pluggable medical condition cartridge to:
perform calculations that are specific to the particular medical condition and a particular candidate treatment, to generate medical condition specific score values; and
apply one or more aggregation operations to one or more subsets of the medical condition specific score values to generate aggregation values, each aggregation value corresponding to one of the set of medical condition independent scoring features of the medical condition independent treatment recommendation model.

7. The method of claim 6, wherein the pluggable medical condition cartridge comprises multiple different instances of medical condition specific evaluation features, each instance being associated with the particular medical condition but being further associated with a different candidate treatment for the particular medical condition.

8. The method of claim 6, wherein the calculations operate on patient factors that provide characteristics of the patient, medical condition factors that characterize the particular medical condition, and candidate treatment factors characterizing aspects of the candidate treatment.

9. The method of claim 6, wherein the calculations operate to evaluate patient specific characteristics, obtained from an electronic medical record associated with the patient, with regard to weighted variables in the set of medical condition specific evaluation features.

10. The method of claim 6, wherein:
each aggregation operation, of the one or more aggregation operations, maps an aggregate value of a subset of the medical condition specific score values to a corresponding medical condition independent scoring feature, of the set of medical condition independent scoring features of the medical condition independent treatment recommendation model.

11. A computer program product comprising a computer readable storage medium having a computer readable program stored therein, wherein the computer readable program, when executed on a computing device, causes the computing device to:

configure, by a medical condition independent score evaluation engine of a medical treatment recommendation system, a medical condition independent treatment recommendation model, wherein the medical condition independent treatment recommendation model is trained on, and operates on, a set of medical condition independent scoring features that are independent of any specific medical condition, wherein the set of medical condition independent scoring features comprise an inclusion criteria score feature, an exclusion criteria score feature, and a preference score feature;

load, by a medical condition cartridge interface of the medical treatment recommendation system, a pluggable medical condition cartridge into a cognitive system to be utilized in a machine learning process to provide a set of medical condition specific evaluation features that are specific to a particular medical condition, wherein the machine learning process that provides the set of medical condition specific evaluation features that are specific to the particular medical condition is trained by the computer readable program further causing the computing device to:
  adjust one or more parameters utilized to evaluate an aggregate of the inclusion criteria score feature, the exclusion criteria score feature, and the preference score feature so as to provide an output as indicated by either a ground truth or golden set of data that not specific to any particular medical condition or particular treatment for a medical condition;

map, by a medical condition independent score feature engine of the medical treatment recommendation system, each of the set of medical condition specific evaluation features to a medical condition independent scoring feature in the set of medical condition independent scoring features;

process, by a medical condition independent score evaluation engine of the medical treatment recommendation engine, patient information for a patient based on application of the mapping of the set of medical condition specific evaluation features, associated with the pluggable medical condition cartridge, and the medical condition independent treatment recommendation model of the medical treatment recommendation system, to generate at least one treatment recommendation for a patient medical condition associated with the patient; and output, by the computing device to a client device, the at least one treatment recommendation for the patient.

12. The computer program product of claim 11, wherein the computer readable program, when executed on a computing device, causes the computing device to:
  generate, for the particular medical condition, at least one medical condition independent scoring feature, of the set of medical condition independent scoring features of the medical condition independent treatment recommendation model, in a manner that is specific to the particular medical condition.

13. The computer program product of claim 11, wherein the computer readable program, when executed on a computing device, causes the computing device to:
  generate at least one medical condition independent scoring feature, of the set of medical condition independent scoring features of the medical condition independent treatment recommendation model, in a manner specific to a combination of the particular medical condition and a candidate treatment.

14. The computer program product of claim 13, wherein the factors comprise one or more factors selected from the set comprising patient factors defining characteristics of the patient and medical condition factors defining characteristics of the patient medical condition.

15. The computer program product of claim 11, wherein the computer readable program further causes the computing device to process patient information for the patient at least by:
  receiving, by the medical treatment recommendation system, an electronic medical record (EMR) of the patient comprising patient factors representing a medical state of the patient;
  executing, by the medical treatment recommendation system, logic that applies at least one of the set of medical condition specific evaluation features of the pluggable medical condition cartridge to generate at least one medical condition independent scoring feature, of the set of medical condition independent scoring features of the medical condition independent treatment recommendation model, for the mapping of the specific medical condition, a candidate treatment, and the patient factors of the patient, based on an aggregation function specified in the pluggable medical condition cartridge; and
  applying, by the medical treatment recommendation system, the medical condition independent treatment recommendation model to the at least one medical condition independent scoring feature to generate a candidate treatment recommendation confidence score for the candidate treatment.

16. The computer program product of claim 11, wherein the computer readable program further causes the computing device to process the patient information comprises executing logic that applies the set of medical condition specific evaluation features of the pluggable medical condition cartridge to:
  perform calculations that are specific to the particular medical condition and a particular candidate treatment, to generate medical condition specific score values; and
  apply one or more aggregation operations to one or more subsets of the medical condition specific score values to generate aggregation values, each aggregation value corresponding to one of the set of medical condition independent scoring features of the medical condition independent treatment recommendation model.

17. The computer program product of claim 16, wherein the pluggable medical condition cartridge comprises multiple different instances of medical condition specific evaluation features, each instance being associated with the particular medical condition but being further associated with a different candidate treatment for the particular medical condition.

18. The computer program product of claim 16, wherein the calculations operate on patient factors that provide characteristics of the patient, medical condition factors that characterize the particular medical condition, and candidate treatment factors characterizing aspects of the candidate treatment.

19. The computer program product of claim 16, wherein:
  each aggregation operation, of the one or more aggregation operations, maps an aggregate value of a subset of the medical condition specific score values to a corresponding medical condition independent scoring feature, of the set of medical condition independent scoring features of the medical condition independent treatment recommendation model.

20. An apparatus comprising:
a processor; and
a memory coupled to the processor, wherein the memory comprises instructions which, when executed by the processor, cause the processor to:
configure, by a medical condition independent score evaluation engine of a medical treatment recommendation system, a medical condition independent treatment recommendation model, wherein the medical condition independent treatment recommendation model is trained on, and operates on, a set of medical condition independent scoring features that are independent of any specific medical condition, wherein the set of medical condition independent scoring features comprise an inclusion criteria score feature, an exclusion criteria score feature, and a preference score feature;
load, by a medical condition cartridge interface of the medical treatment recommendation system, a pluggable medical condition cartridge into a cognitive system to be utilized in a machine learning process to provide a set of medical condition specific evaluation features that are specific to a particular medical condition, wherein the machine learning process that provides the set of medical condition specific evaluation features that are specific to the particular medical condition is trained by the instructions further causing the processor to:
adjust one or more parameters utilized to evaluate an aggregate of the inclusion criteria score feature, the exclusion criteria score feature, and the preference score feature so as to provide an output as indicated by either a ground truth or golden set of data that not specific to any particular medical condition or particular treatment for a medical condition;
map, by a medical condition independent score feature engine of the medical treatment recommendation system, each of the set of medical condition specific evaluation features to a medical condition independent scoring feature in the set of medical condition independent scoring features;
process, by a medical condition independent score evaluation engine of the medical treatment recommendation engine, patient information for a patient based on application of the mapping of the set of medical condition specific evaluation features, associated with the pluggable medical condition cartridge, and the medical condition independent treatment recommendation model of the medical treatment recommendation system, to generate at least one treatment recommendation for a patient medical condition associated with the patient; and
output, by the processor to a client device, the at least one treatment recommendation for the patient.

* * * * *